United States Patent
Sankaran et al.

(10) Patent No.: US 10,315,978 B2
(45) Date of Patent: Jun. 11, 2019

(54) METHOD OF PRODUCING TEREPHTHALIC ACID

(71) Applicant: SABIC GLOBAL TECHNOLOGIES B.V., Bergen op Zoom (NL)

(72) Inventors: Nedumbamana Sankaran, Riyadh (SA); Syed Azhar Hashmi, Riyadh (SA); Vinodkumar Vasudevan, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/775,874

(22) PCT Filed: Nov. 14, 2016

(86) PCT No.: PCT/IB2016/056833
§ 371 (c)(1),
(2) Date: May 14, 2018

(87) PCT Pub. No.: WO2017/085608
PCT Pub. Date: May 26, 2017

(65) Prior Publication Data
US 2018/0319732 A1 Nov. 8, 2018

Related U.S. Application Data

(60) Provisional application No. 62/255,659, filed on Nov. 16, 2015.

(51) Int. Cl.
*C07C 51/487* (2006.01)
*C07C 1/12* (2006.01)

(52) U.S. Cl.
CPC .............. *C07C 51/487* (2013.01); *C07C 1/12* (2013.01)

(58) Field of Classification Search
CPC .............................. C07C 51/487; C07C 1/12
USPC ....... 562/409, 412, 487, 608, 480, 414, 416, 562/486, 607, 405, 481, 482; 528/271
See application file for complete search history.

(56) References Cited

U.S. PATENT DOCUMENTS

| 3,728,339 A * | 4/1973 | Bode et al. .......... C07D 249/18 548/224 |
| 4,260,817 A | 4/1981 | Thompson et al. |
| 4,415,479 A | 11/1983 | Puskas et al. |
| 4,939,297 A | 7/1990 | Browder et al. |
| 5,185,370 A | 2/1993 | Backstrom et al. |
| 5,929,274 A | 7/1999 | Lamshing et al. |
| 7,132,566 B2 | 11/2006 | Sumner, Jr. et al. |
| 2005/0228195 A1 | 10/2005 | Wytcherley et al. |
| 2005/0260144 A1 | 11/2005 | Huber |
| 2014/0121406 A1 * | 5/2014 | McDonnell .......... C07C 51/265 562/413 |
| 2014/0171680 A1 | 6/2014 | Buchbinder et al. |

FOREIGN PATENT DOCUMENTS

CN 102174035 A 9/2011

OTHER PUBLICATIONS

International Search Report for International Application No. PCT/IB2016/056833; International Filing Date: Nov. 14, 2016; dated Feb. 8, 2017; 5 Pages.
Liu et al., "Asymmetric Michael Addition of Ketones to Aklylidene Malonates and Allylidene Malonates via Enamne—Metal Lewis Acid Bifunctional Catalysis," The Journal of Organic Chemistry, vol. 77 (2012) pp. 7693-7699.
Stanchev et al., "Synthesis, computational study and cytotoxic activity of new 4-hydroxycoumarin derivatives," European Journal of Medicinal Chemistry, vol. 43 (2008), pp. 694-706.
Written Opinion for International Application No. PCT/IB2016/056833; International Filing Date: Nov. 14, 2016; dated Feb. 8, 2017; 5 Pages.
Zhang et al., "Selection, synthesis, and anti-inflammatory evaluation of the arylidene malonate derivatives as TLR4 signaling inhibitors," Bioorganic & Medicinal Chemistry, vol. 20 (2012), pp. 6073-6079.
Machine Translation of CN102174035(A); Date of Publication: Sep. 7, 2011; 33 Pages.

* cited by examiner

*Primary Examiner* — Yevgeny Valenrod
(74) *Attorney, Agent, or Firm* — Cantor Colburn LLP

(57) ABSTRACT

A method of reducing the formation of an impurity in a terephthalic acid (TPA) production process includes: combining in a reactor, a catalyst, a mixture comprising the impurity and the TPA, and a compound comprising an active carbon atom; reacting the impurity with the compound in the presence of the catalyst by a condensation-dehydration reaction process comprising a nucleophilic addition of the active carbon atom of the compound to a carbonyl group of the impurity to form an intermediate followed by a dehydration reaction of the intermediate to form a product mixture comprising a water, the TPA, and an alkene; and recovering the product mixture from the reactor.

19 Claims, No Drawings

METHOD OF PRODUCING TEREPHTHALIC ACID

CROSS REFERENCE TO RELATED APPLICATIONS

This application is a 371 of International Application No. PCT/IB2016/056833, filed Nov. 14, 2016, which claims priority to U.S. Application Ser. No. 62/255,659 filed Nov. 16, 2015, which are incorporated herein by reference in their entirety.

BACKGROUND

Purified carboxylic acids, particularly aromatic dicarboxylic, acids are industrially important chemicals. For example, polymer grade benzene-1,4-dicarboxylic acid (also referred to as terephthalic acid or TPA) of chemical formula $C_6H_4(COOH)_2$ can be a starting material for the formation of polyester resin, which can be used to make many materials of commerce having a variety of utilities.

The production of TPA can include liquid phase oxidation of an aromatic hydrocarbon. This process, however, can result in a product which includes impurities such as 4-carboxybenzaldehyde (4-CBA). The amount of 4-CBA produced by this process can be 1,000 parts per million to 10,000 parts per million. These impurities are undesirable as they can include chain termination agents, colored impurities, and other reaction by-products. Because these impurities affect product quality (e.g., color, material properties, and the like) they reduce the value of the TPA product if not removed. As a result, the crude TPA often undergoes cumbersome purification processes.

Thus, there remains a desire in industrial production of TPA to reduce or eliminate the production of impurities and/or to simplify the TPA production process.

SUMMARY

Disclosed, in various embodiments, are methods of reducing the formation of an impurity in a terephthalic acid (TPA) production process.

A method of reducing the formation of an impurity in a terephthalic acid (TPA) production process comprises: combining in a reactor, a catalyst, a mixture comprising the impurity and the TPA, and a compound comprising an active carbon atom; wherein the impurity comprises formula (I); $R_1$-Bn-COH (I) wherein $R_1$ comprises a hydrogen atom, an alkyl, carboxyl, carbonyl, aldehyde, ether, ester, alkynyl, alkenyl, halo, hydroxyl, haloformyl, carbonate ester, carboxylate, peroxy, acetal, a nitrogen containing functional group, a sulfur containing functional group, a phosphorous containing functional group, or a combination comprising at least one of the foregoing; wherein Bn is a benzene ring; and wherein COH is an aldehyde group; wherein the compound comprises formula (II), (III), or (IV); $Z_1$—$CH_2$—$Z_2$ (II) $Z_1$—$CHR_2$—$Z_2$ (III) $Z_1$—$CHR_2R_3$ (IV) wherein $Z_1$ and $Z_2$ each comprise an electron withdrawing functional group, and wherein $R_2$ and $R_3$ each comprise an atom of carbon, hydrogen, oxygen, nitrogen, sulfur, or a combination comprising at least one of the foregoing; reacting the impurity with the compound in the presence of the catalyst by a condensation-dehydration reaction process comprising a nucleophilic addition of the active carbon atom of the compound to a carbonyl group of the impurity to form an intermediate followed by a dehydration reaction of the intermediate to form a product mixture comprising a water, the TPA, and an alkene comprising formula (V), (VI), or (VII); $R_4$-Bn-$C_2Z_1Z_2$ (V) $R_4$-Bn-$C_2Z_1R_2Z_2$ (VI) $R_4$-Bn-$C_2Z_1R_2R_3$ (VII) wherein $R_4$ comprises $R_1$ or COH; and recovering the product mixture from the reactor.

These and other features and characteristics are more particularly described below.

DETAILED DESCRIPTION

A dicarboxylic acid production process can include liquid phase oxidation of an aromatic hydrocarbon, such as a xylene. For example, in an embodiment the process can include the production of terephthalic acid (TPA). The TPA production process can include liquid phase oxidation of 1,4-dimethylbenzene (p-xylene) with air. The oxidation can be catalytic, such as in the presence of a catalyst including one or more of cobalt, manganese, and bromide ions in a solvent (e.g., acetic acid). The oxidation can be performed at elevated temperatures and pressures, e.g., at a temperature of 170° C.-210° C. and at a pressure of 15-30 bar, for example, 10-30 bar. Once the oxidation is complete the TPA can be crystallized and filtered to form a crude TPA product. Impurities in the crude TPA produced in this way can include molecules of formula (I):

$R_1$-Bn-COH    (I)

where, $R_1$ can include a hydrogen atom, an alkyl, carboxyl, carbonyl, aldehyde, ether, ester, alkynyl, alkenyl, halo, hydroxyl, haloformyl, carbonate ester, carboxylate, peroxy, acetal, a nitrogen containing functional group, a sulfur containing functional group, a phosphorous containing functional group, or a combination comprising at least one of the foregoing; Bn represents a benzene ring; and COH represents an aldehyde group. The position of substituent $R_1$ relative to the aldehyde substituent group (COH) can be ortho (1,2), meta (1,3), or para (1,4) on the benzene ring. For example, impurities can include 4-carboxybenzaldehyde (4-CBA), 3-carboxybenzaldehyde (3-CBA), 2-carboxybenzaldehyde (2-CBA), 4-methylbenzoic acid (p-toluic acid), 3-methylbenzoic acid (m-toluic acid), 2-methylbenzoic acid (o-toluic acid), colored impurities, or a combination including at least one of the foregoing.

These impurities can affect the material properties (e.g., color, shear strength, tensile strength, flexural modulus, glass transition temperature, and the like) of any polymer derived from the crude TPA product. For example, impurities such as 4-CBA can act as a chain termination agent during polymerization which can alter the mechanical strength in comparison to polymers derived from pure TPA having no impurities. Furthermore, because impurities such as 4-CBA can co-crystalize with TPA it can be difficult to remove them from the crude TPA which can result in reduced process efficiency, additional waste streams, increased cost (e.g., processing cost, capital cost, or both), or a combination including at least one of the foregoing. Before purification, the amount of 4-CBA in the TPA product can be 1,000 ppm to 10,000 ppm.

The crude TPA can be subjected to a purification process to reduce the amount (e.g., mole percent) of impurities in the crude TPA and to yield a polymer grade TPA product (e.g., such as containing less than or equal to 25 parts per million by weight (ppmw) of 4-CBA). The purification process can include hydrogenation, centrifugation, crystallization, filtration, washing, or a combination including at least one of the foregoing. For example, the crude TPA can be dissolved in hot water where impurities (e.g., 4-CBA) can be reduced in the presence of a palladium catalyst and recovered as p-toluic acid. However, such a purification process can be undesirable from an engineering and/or economic standpoint as it can increase the manufacturing cost, reduce throughput, reduce production efficiency, and/or result in an added waste stream. Because of the huge production capacity of polymer grade TPA, improvements in the process and reduction of the amount of impurities can have a large economic value.

Disclosed herein is a method of reducing the formation of impurities in a TPA production process. The method can include combining a catalyst, a mixture containing an impurity of formula (I) and TPA, and a compound containing an active carbon atom. The method can include reacting the impurity with the compound having the active carbon atom in the presence of the catalyst by a condensation reaction process (e.g., a Knoevenagel condensation process, an aldol condensation process, or the like). The condensation reaction process can include a nucleophilic addition of the active carbon of the compound to a carbonyl group of the impurity followed by a dehydration reaction to form a raw product stream containing the TPA, water, and an alkene. The method can include recovering the product mixture from the reactor. The product mixture can be separated into a by-product and a product. The by-product can include the alkene, water, or a combination including at least one of the foregoing. The product can include the TPA, the alkene, or a combination including at least one of the foregoing.

The product can be a polymer grade TPA. Polymer grade TPA meets the following specifications.

| Property | Specification | Test Method |
|---|---|---|
| Acid Number | 675 ± 2 mgKOH/g | Titration (ASTM D974) |
| Ash | ≤15 ppm | Pyrolysis |
| Total metals (Mo, Cr, Ni, Co, Fe, Ti, Mg) | 10 ppm | ICP |
| 4-CBA content | ≤25 ppm | Polarography |
| Moisture content | ≤0.5 wt % | Karl Fischer |
| 5% dimethyl formamide solution color (ALPHA) | ≤10 | Colorimetry (ASTM E1347) | mgKOH/g = milligrams potassium hydroxide per gram of product;
ppm = parts per million by weight;
≤ is less than or equal to.
ICP = inductively coupled plasma The condensation reaction process of the compound and the impurity can be carried out in the presence of a catalyst. The condensation reaction process can be carried out at a temperature of 10° C. to 300° C., for example 15° C. to 275° C., or, 25° C. to 250° C., or 35° C. to 200° C. The condensation reaction process can be carried out at a gauge pressure of 0 megaPascal (MPa) to 5 MPa, or 0.1 MPa to 5 MPa, or 0.2 MPa to 2 MPa.

The compound can contain an active carbon atom and one or more adjacent electron withdrawing functional groups. The electron withdrawing functional group can include any functional group which draws electrons away from the active carbon atom. For example, the electron withdrawing functional group can include, but is not limited to, a carbonyl, cyanate, ester, halogen, nitrate, nitrile, nitrite, nitro, and the like. Examples of possible compounds with an active carbon atom include, 1,3-cyclohexanedione, pentane-2,4-dione (acetylacetone), ethyl acetoacetate, propane dioic acid (malonic acid), 1,3-diethyl propanedioate (diethyl malonate), pyrimidine-2,4,6(1H,3H,5H)-trione (barbituric acid), 1,3-dicyclopropane propane-1,3-dione, 3-oxobutane-1-nitrile, and 1-nitropropan-2-one.

The electron withdrawing functional group can include any atom, molecule, or functional group that results in the compound having a logarithmic acid dissociation constant ($pK_a$) of less than or equal to 45 in dimethyl sulfide as measured according to known testing methods, such as titration. For example, the $pK_a$ of the compound can be less than or equal to 45, or, −10 to 45, or, −10 to 40, or 0 to 35. The acid dissociation constant ($K_a$) is a quantitative measure of the equilibrium concentration of the conjugate base and the proton (dissociated from the active carbon atom) relative to the concentration of the compound (i.e., $K_a = [A^-][H^+]/[HA]$, where A represents the conjugate base of the acid). The logarithmic acid dissociation constant ($pK_a$) is related to the acid dissociation constant ($K_a$) by the relation $pK_a = -\log_{10}(K_a)$.

As disclosed herein, compounds having an active carbon atom can include compounds of a formula (II), (III), or (IV):

  (II)

  (III)

  (IV)

where $Z_1$ and $Z_2$ contain an electron withdrawing functional group, and where $R_2$ and $R_3$ contain an atom of carbon, hydrogen, oxygen, nitrogen, sulfur, or a combination comprising at least one of the foregoing. It should be noted that $R_2$ and $R_3$ can have the same chemical structure, chemical formula, or both (e.g., $R_2$ and $R_3$ can each be $CH_3$) or can have differing chemical structure, chemical formula, or both (e.g., $R_2$=$COOC_2H_5$ and $R_3$=H). It should also be noted that $Z_1$ and $Z_2$ can each have the same chemical structure, chemical formula, or both (e.g., $Z_1$ and $Z_2$ can each be $COCH_3$) or can have a different chemical structure, chemical formula, or both (e.g., $Z_1$=$COCH_3$ and $Z_2$=$CN$). Furthermore, $Z_1$ and $Z_2$ can join to form a cyclic compound (e.g., cyclohexane-1,3-dione). These compounds can form nucleophilic intermediates when a proton dissociates (from the active carbon atom) and an unshared pair of electrons is retained by the active carbon atom.

The Applicant is not required to provide a description of the theory of operation of the invention and the appended claims should not be limited by Applicant's statements regarding such theory, but it is thought that the method can include a nucleophilic addition followed by a dehydration reaction, such as in a Knoevenagel condensation reaction process. The nucleophilic addition can include bonding of the active carbon of the compound to a carbonyl group of the impurity. During the nucleophilic addition, nucleophilic intermediates can be formed (such as catalytically) which can bond to a carbon atom of a carbonyl group of the impurity. For example, the nucleophilic intermediate can bond to carbon atom of a carbonyl of an aldehyde functional group of the impurity (e.g., 4-CBA, 3-CBA, 2-CBA, or other aldehyde containing impurity). Such nucleophilic addition can result in sigma and pi bonds (double bonds) between the active carbon and the carbon of the carbonyl of the impurity. The dehydration reaction can include formation of a water molecule which can include the oxygen atom from the carbonyl of the impurity, and can result in the formation of an alkene and the water molecule.

The catalyst can be used to promote the condensation and/or dehydration process. The catalyst can promote nucleophilic addition, such as by dissociating the compound to a proton and its conjugate base (nucleophilic intermediate). Any suitable catalyst or catalytic mixture can be used including an acid, base, ionic liquid, halogen, metal or a combination including at least one of the forgoing. The catalyst can include an acid, such as a carboxylic acid (e.g., trifluoroacetic acid, acetic acid, and the like), sulfonic acid (e.g. toluenesulfonic acid), alcohol, thiol, enol, phenol, or a combination including at least one of the forgoing. The catalyst can include bases, such as an organic base (e.g. piperidine) The catalyst can include a solvent, such as a non-polar solvent, polar aprotic solvent, polar protic solvent, or a combination including at least one of the foregoing. For example, a solvent can include thionyl chloride, dimethyl sulfoxide, acetone, ethyl acetate, tetrahydrofuran, dichloromethane, dimethylformamide, acetonitrile, propylene carbonate, methanol, ethanol, or a combination including at least one of the foregoing. The catalyst can include a halogen (e.g., bromine, chlorine, iodine, fluorine, and the like), which can be in ionic form in a catalytic mixture. The catalyst can include a metal (e.g. zinc chloride, ferric chloride). The metal can include an element from any of Groups 3-12 of the periodic table, a lanthanide, an actinide, or a combination including at least one of the foregoing. The metal can be a transition metal. The metal can include cobalt and manganese. The nucleophilic addition can be catalyzed by acids, bases, solvents, metals, or a combination comprising at least one of the foregoing.

Combining as used herein includes bringing together two or more elements (e.g., catalyst, mixture, and compound). The two or more elements can be combined outside or inside the boundary of a unit (e.g., a vessel, reactor, separator, recovery device, and the like). For example, combining can include joining two or more conduits, each conveying a process stream, into a single conduit (e.g., manifold, reactor, pipe, vessel, and the like), or can include adding elements separately in serial fashion to a vessel. Combining includes, but is not limited to, mixing the elements, as in static or dynamic mixing of the combined elements. It should be understood to those of skill in the art that combining can be done in a flow process, a continuous process, in a batch process, a discrete process, or a combination including at least one of the foregoing.

The alkene formed during the disclosed process can include an alkene of any one of the formulas (V), (VI), or (VII):

  (V)

  (VI)

  (VII)

where $Z_1$, $Z_2$, $R_2$, $R_3$, are as have been described in the foregoing, and where $R_4$ comprises an aldehyde substituent (COH) or $R_1$ as described in the foregoing. The alkene can include any alkene derived from chemical reaction between the active carbon atom containing compound and the impurity. For example, the compound having the active carbon atom can include pentane-2,4-dione (also referred to as acetylacetone or hacac) which can react with 4-CBA to form a 4-(2-acetyl-3-oxobut-1-en-1-yl) benzoic acid. In this case, the compound corresponds to formula (II) and the alkene corresponds to formula (V), where $Z_1$ and $Z_2$ are both $COCH_3$ and the active carbon atom is carbon number 3 of the pentane backbone of the pentane-2,4-dione which is disposed between two carbonyl groups.

Subjecting a mixture of TPA and an impurity (where the impurity concentration exceeds the specification of polymer grade TPA), to the disclosed method can reduce the impurity concentration of the mixture to polymer grade TPA levels (e.g., less than or equal to 25 ppmw) without the need for purification steps including hydrogenation, centrifugation, crystallization, filtration, washing, or a combination including at least one of the foregoing. Thus, the disclosed method can increase production efficiency, increase throughput, decrease production cost, eliminate waste, or a combination including at least one of the foregoing.

In an embodiment the alkene produced by the disclosed method can include a fluorescent alkene, such as oxazole. In this way the alkene can include a desirable molecule which can advantageously be retained in the TPA product. Such a desirable molecule can reduce or eliminate the need for additional optical brighteners or other additives which can be added to the polymer grade TPA prior to or during polymerization. This can eliminate the need for additional optical brighteners or other additives and provide a streamlined process free of such additions.

TPA produced by the foregoing methods can be used in the production of a polymer. For example, TPA can be used as a starting material in the production of polyesters (e.g., including poly(ethylene terephthalate) (PET), polybutylene terephthalate (PBT), and polytrimethylene terephthalate (PTT)), polyphthalamides, or a combination comprising at least one of the foregoing. The polymer can be a dendrimer. The polymer can be linear, branched, or a combination comprising at least one of the foregoing. The polymer can include a homopolymer or copolymer comprising units of two or more of the foregoing polymers. The copolymers can be random, alternating, graft, and block copolymers having two or more blocks of different homopolymers, random, or alternating copolymers.

The methods of reducing the formation of an impurity in a terephthalic acid (TPA) production process disclosed herein include(s) at least the following embodiments:

Embodiment 1

A method of reducing the formation of an impurity in a terephthalic acid (TPA) production process comprising: combining in a reactor, a catalyst, a mixture comprising the impurity and the TPA, and a compound comprising an active carbon atom; wherein the impurity comprises formula (I); $R_1$-Bn-COH (I) wherein $R_1$ comprises a hydrogen atom, an alkyl, carboxyl, carbonyl, aldehyde, ether, ester, alkynyl, alkenyl, halo, hydroxyl, haloformyl, carbonate ester, carboxylate, peroxy, acetal, a nitrogen containing functional group, a sulfur containing functional group, a phosphorous containing functional group, or a combination comprising at least one of the foregoing; wherein Bn is a benzene ring; and wherein COH is an aldehyde group; wherein the compound comprises formula (II), (III), or (IV); $Z_1$—$CH_2$—$Z_2$ (II) $Z_1$—$CHR_2$—$Z_2$ (III) $Z_1$—$CHR_2R_3$ (IV) wherein $Z_1$ and $Z_2$ each comprise an electron withdrawing functional group, and wherein $R_2$ and $R_3$ each comprise an atom of carbon, hydrogen, oxygen, nitrogen, sulfur, or a combination comprising at least one of the foregoing; reacting the impurity with the compound in the presence of the catalyst by a condensation-dehydration reaction process comprising a nucleophilic addition of the active carbon atom of the compound to a carbonyl group of the impurity to form an intermediate followed by a dehydration reaction of the intermediate to form a product mixture comprising a water, the TPA, and an alkene comprising formula (V), (VI), or (VII); $R_4$-Bn-$C_2Z_1Z_2$ (V) $R_4$-Bn-$C_2Z_1R_2Z_2$ (VI) $R_4$-Bn-$C_2Z_1R_2R_3$ (VII) wherein $R_4$ comprises $R_1$ or COH; and recovering the product mixture from the reactor.

Embodiment 2

The method of Embodiment 1, further comprising separating the product mixture to form a by-product comprising greater than or equal to 0.01 wt % of the alkene and greater than or equal to 0.01 wt % of the water, and a product comprising greater than or equal to 99.9 wt % of the TPA, wherein the weight percentages are based upon a total weight of the product mixture.

Embodiment 3

The method of Embodiment 1, further comprising separating the product mixture to form a by-product comprising greater than or equal to 0.01 wt % of the water, and a product comprising greater than or equal to 0.01 wt % of the TPA and greater than or equal to 99.9 wt % of the alkene, wherein the weight percentages are based upon a total weight of the product mixture.

Embodiment 4

The method of any of Embodiments 2-3, wherein a concentration of the impurity in the product is less than or equal to 25 ppmw.

Embodiment 5

The method of Embodiment 4, wherein the impurity is 4-CBA.

Embodiment 6

The method of any of Embodiments 1-5, further comprising recycling the product mixture to a second reactor.

Embodiment 7

The method of any of Embodiments 1-6, wherein the alkene comprises a fluorescent functional group.

Embodiment 8

The method of any of Embodiments 1-7, wherein the TPA production process is free of a hydrogenation process and the impurity is not hydrogenated.

Embodiment 9

The method of any of Embodiments 1-8, wherein the active carbon atom is of formula (II) or (III), and wherein $Z_1$ and $Z_2$ comprise the same molecular formula.

Embodiment 10

The method of any of Embodiments 1-9, wherein the active carbon atom is of formula (IV), and wherein $R_2$ and $R_3$ comprise the same molecular formula.

Embodiment 11

The method of any of Embodiments 1-10, wherein the catalyst comprises an acid, a base, a solvent, a metal, a halogen, or a combination comprising at least one of the forgoing.

Embodiment 12

The method of any of Embodiments 1-11, wherein the catalyst comprises an acid, a cobalt, a manganese, a bromide, a solvent, or a combination comprising at least one of the forgoing.

Embodiment 13

The method of any of Embodiments 1-12, further comprising washing the product mixture with heated water.

Embodiment 14

The method of any of Embodiments 1-13, wherein a concentration of the impurity in the product mixture is less than or equal to 25 ppmw.

Embodiment 15

The method of Embodiment 14, wherein the impurity is 4-CBA.

Embodiment 16

The method of any of Embodiments 1-15, wherein the electron withdrawing functional group comprises carbonyl, cyanate, ester, halogen, nitrate, nitrile, nitrite, nitro, or a combination comprising at least one of the foregoing.

Embodiment 17

The method of any or Embodiments 1-16, wherein the impurity comprises 4-carboxybenzaldehyde, 3-carboxybenzaldehyde, 2-carboxybenzaldehyde, 4-methylbenzoic acid (p-toluic acid), 3-methylbenzoic acid (m-toluic acid), 2-methylbenzoic acid (o-toluic acid), colored impurities, or a combination comprising at least one of the foregoing.

Embodiment 18

The method of any or Embodiments 1-17, wherein the impurity comprises 4-carboxybenzaldehyde, 4-methylbenzoic acid (p-toluic acid), or a combination comprising at least one of the foregoing.

Embodiment 19

The method of any of Embodiments 1-18, further comprising polymerizing the TPA to form a polymer.

Embodiment 20

An article made from the polymer of Embodiment 19.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

We claim:

1. A method of reducing the formation of an impurity in a terephthalic acid (TPA) production process comprising:
   combining in a reactor, a catalyst, a mixture comprising the impurity and the TPA, and a compound comprising an active carbon atom;
   wherein the impurity comprises formula (I);

$$R_1\text{-Bn-COH} \qquad (I)$$

wherein $R_1$ comprises a hydrogen atom, an alkyl, carboxyl, carbonyl, aldehyde, ether, ester, alkynyl, alkenyl, halo, hydroxyl, haloformyl, carbonate ester, carboxylate, peroxy, acetal, a nitrogen containing functional group, a sulfur containing functional group, a phosphorous containing functional group, or a combination comprising at least one of the foregoing;
   wherein Bn is a benzene ring; and
   wherein COH is an aldehyde group;
   wherein the compound comprises formula (II), (III), or (IV);

$$Z_1\text{—}CH_2\text{—}Z_2 \qquad (II)$$

$$Z_1\text{—}CHR_2\text{—}Z_2 \qquad (III)$$

$$Z_1\text{—}CHR_2R_3 \qquad (IV)$$

wherein $Z_1$ and $Z_2$ each comprise an electron withdrawing functional group, and
   wherein $R_2$ and $R_3$ each comprise an atom of carbon, hydrogen, oxygen, nitrogen, sulfur, or a combination comprising at least one of the foregoing;
   reacting the impurity with the compound in the presence of the catalyst by a condensation-dehydration reaction process comprising a nucleophilic addition of the active carbon atom of the compound to a carbonyl group of the impurity to form an intermediate followed by a dehydration reaction of the intermediate to form a product mixture comprising a water, the TPA, and an alkene comprising formula (V), (VI), or (VII);

$$R_4\text{-Bn-}C_2Z_1Z_2 \qquad (V)$$

$$R_4\text{-Bn-}C_2Z_1R_2Z_2 \qquad (VI)$$

$$R_4\text{-Bn-}C_2Z_1R_2R_3 \qquad (VII)$$

wherein $R_4$ comprises $R_1$ or COH; and
   recovering the product mixture from the reactor.

2. The method of claim 1, further comprising separating the product mixture to form a by-product comprising greater than or equal to 0.01 wt % of the alkene and greater than or equal to 0.01 wt % of the water, and a product comprising greater than or equal to 99.9 wt % of the TPA, wherein the weight percentages are based upon a total weight of the product mixture.

3. The method of claim 1, further comprising separating the product mixture to form a by-product comprising greater than or equal to 0.01 wt % of the water, and a product comprising greater than or equal to 0.01 wt % of the TPA and greater than or equal to 99.9 wt % of the alkene, wherein the weight percentages are based upon a total weight of the product mixture.

4. The method of claim 1, wherein a concentration of the impurity in the product is less than or equal to 25 ppmw.

5. The method of claim 4, wherein the impurity is 4-CBA.

6. The method of claim 1, further comprising recycling the product mixture to a second reactor.

7. The method of claim 1, wherein the alkene comprises a fluorescent functional group.

8. The method of claim 1, wherein the TPA production process is free of a hydrogenation process and the impurity is not hydrogenated.

9. The method of claim 1, wherein the active carbon atom is of formula (II) or (III), and wherein $Z_1$ and $Z_2$ comprise the same molecular formula.

10. The method of claim 1, wherein the active carbon atom is of formula (IV), and wherein $R_2$ and $R_3$ comprise the same molecular formula.

11. The method of claim 1, wherein the catalyst comprises an acid, a base, a solvent, a metal, a halogen, or a combination comprising at least one of the forgoing.

12. The method of claim 1, wherein the catalyst comprises an acid, a cobalt, a manganese, a bromide, a solvent, or a combination comprising at least one of the forgoing.

13. The method of claim 1, further comprising washing the product mixture with heated water.

14. The method of claim 1, wherein a concentration of the impurity in the product mixture is less than or equal to 25 ppmw.

15. The method of claim 14, wherein the impurity is 4-CBA.

16. The method of claim 1, wherein the electron withdrawing functional group comprises carbonyl, cyanate, ester, halogen, nitrate, nitrile, nitrite, nitro, or a combination comprising at least one of the foregoing.

17. The method of claim 1, wherein the impurity comprises 4-carboxybenzaldehyde, 3-carboxybenzaldehyde, 2-carboxybenzaldehyde, 4-methylbenzoic acid (p-toluic acid), 3-methylbenzoic acid (m-toluic acid), 2-methylbenzoic acid (o-toluic acid), colored impurities, or a combination comprising at least one of the foregoing.

18. The method of claim 1, wherein the impurity comprises 4-carboxybenzaldehyde, 4-methylbenzoic acid (p-toluic acid), or a combination comprising at least one of the foregoing.

19. The method of claim 1, further comprising polymerizing the TPA to form a polymer.

* * * * *